United States Patent
Keenan et al.

(10) Patent No.: US 10,899,913 B2
(45) Date of Patent: Jan. 26, 2021

(54) AIR TREATMENT AND LONG TERM FRAGRANCE RELEASE GEL

(71) Applicants: Rohm and Haas Company, Collegeville, PA (US); Union Carbide Corporation, Seadrift, TX (US)

(72) Inventors: Andrea C. Keenan, Pottstown, PA (US); Emmett M. Partain, III, Bound Brook, NJ (US); Theodore Tysak, Ambler, PA (US); Jennifer J. Todd, Willow Grove, PA (US)

(73) Assignees: Rohm and Haas Company, Philadelphia, PA (US); Union Carbide Corporation, Seadrift, TX (US)

(*) Notice: Subject to any disclaimer, the term of this patent is extended or adjusted under 35 U.S.C. 154(b) by 199 days.

(21) Appl. No.: 16/088,838

(22) PCT Filed: Mar. 29, 2017

(86) PCT No.: PCT/US2017/024759
§ 371 (c)(1),
(2) Date: Sep. 27, 2018

(87) PCT Pub. No.: WO2017/176526
PCT Pub. Date: Oct. 12, 2017

(65) Prior Publication Data
US 2020/0148859 A1     May 14, 2020

Related U.S. Application Data

(60) Provisional application No. 62/319,028, filed on Apr. 6, 2016.

(51) Int. Cl.
*C08L 5/04* (2006.01)
*C08L 1/28* (2006.01)
*C08J 3/075* (2006.01)
*A61L 9/04* (2006.01)
*A61L 9/012* (2006.01)

(52) U.S. Cl.
CPC ............... *C08L 5/04* (2013.01); *C08J 3/075* (2013.01); *C08L 1/286* (2013.01); *A61L 9/012* (2013.01); *A61L 9/048* (2013.01); *C08J 2305/04* (2013.01); *C08J 2401/02* (2013.01)

(58) Field of Classification Search
None
See application file for complete search history.

(56) References Cited

U.S. PATENT DOCUMENTS

| 4,125,478 A | 11/1978 | Sullivan et al. |
| 5,541,234 A * | 7/1996 | Unger ............. B01J 20/24 521/141 |
| 7,488,471 B2 * | 2/2009 | Mercier ............ A61K 8/062 424/401 |
| 2005/0037080 A1 | 2/2005 | Lynch et al. |
| 2012/0230936 A1 | 9/2012 | Mikkelsen |
| 2013/0157922 A1 | 6/2013 | Mikkelsen et al. |
| 2014/0158788 A1 | 6/2014 | Mikkelsen et al. |
| 2015/0231295 A1 | 8/2015 | Yun et al. |

FOREIGN PATENT DOCUMENTS

| WO | 0140370 | 6/2001 |
| WO | 03090718 | 11/2003 |
| WO | 2011008365 | 1/2011 |
| WO | 2012051131 | 4/2012 |
| WO | 2014063358 | 5/2014 |

* cited by examiner

*Primary Examiner* — Eric Olson
(74) *Attorney, Agent, or Firm* — Kenneth Crimaldi

(57) ABSTRACT

A method for producing a crosslinked gel. The method comprises steps of: (a) combining (i) water, (ii) alginic acid, alginates, or mixtures thereof, (iii) carboxymethylcellulose, (iv) a salt of calcium, magnesium or zinc, (v) a nonionic surfactant and (vi) fragrance to form a gel having a surface; and (b) contacting with the surface of said gel an additional aqueous solution of a salt of calcium, magnesium or zinc.

6 Claims, No Drawings

AIR TREATMENT AND LONG TERM FRAGRANCE RELEASE GEL

This invention relates to a method for producing a crosslinked gel comprising fragrance.

Gels consist of a solid three-dimensional network that spans the volume of a liquid medium and ensnares it through surface tension effects. This internal network structure may result from physical bonds (physical gels) or chemical bonds (chemical gels), as well as crystallites or other junctions that remain intact within the extending fluid. Gels have been used as vehicles for fragrance delivery, as in, e.g., US2015/0231295. However, this reference does not suggest the method described herein.

The problem solved by this invention is the need for improved controlled release of fragrances.

STATEMENT OF INVENTION

The present invention provides a method for producing a crosslinked gel; said method comprising steps of: (a) combining (i) water, (ii) alginic acid, alginates, or mixtures thereof, (iii) carboxymethylcellulose, (iv) a salt of calcium, magnesium or zinc, (v) a nonionic surfactant and (vi) fragrance to form a gel having a surface; and (b) contacting with the surface of said gel an aqueous solution of a salt of calcium, magnesium or zinc.

DETAILED DESCRIPTION

Percentages are weight percentages (wt. %) and temperatures are in ° C., unless specified otherwise. Operations were performed at room temperature (20-25° C.), unless specified otherwise. Percentages of gel components are based on the entire weight of the gel. A "gel" is a mixture of ingredients which will spontaneously form a gel or the formed gel.

A "fragrance" includes any hydrophobic component which provides a pleasant scent. Examples include scents that are floral, ambery, woody, leather, chypre, fougere, musk, vanilla, fruit, and/or citrus. Fragrance oils are obtained by extraction of natural substances or synthetically produced. Fragrances produced may be simple (one essence) or complex (a mélange of essences). Often, the fragrance oils are accompanied by auxiliary materials, such as fixatives, extenders, stabilizers and solvents.

Preferably, the carboxymethylcellulose has a molar degree of substitution $MS_{carboxy}$ from 0.3 to 1.8, preferably at least 0.5, preferably at least 0.6; preferably no more than 1.6, preferably no more than 1.5, preferably no more than 1.4. Typically, viscosities of 1% by weight aqueous carboxymethylcellulose solutions at 20° C., determined with a Brookfield viscometer, range from 20 to 50000 mPa·s, preferably from 500 to 2000 mPa·s, and more preferably from 2000 to 10000 mPa·s. Examples of commercially available carboxymethylcellulose that are useful in the present invention include WALOCEL™ CRT 50000 PA ($MS_{carboxy}$=0.7, 1% by weight Brookfield viscosity=7000 mPa·s), and more preferably WALOCEL™ CRT 30000 ($MS_{carboxy}$=0.9, 1% by weight Brookfield viscosity=3500 mP·s), available from The Dow Chemical Company, Midland, U.S.A. Preferably, carboxymethylcellulose is used in the form of the sodium salt.

Preferably, the composition is substantially free of any cellulose derivative other than carboxymethylcellulose, i.e., the total amount of other cellulose derivatives is no greater than 5 wt % of total weight of cellulose derivatives, preferably no greater than 2 wt %, preferably no greater than 1 wt %, preferably no greater than 0.5 wt %.

Preferably, the gel comprises alginic acid, alginates, or mixtures thereof. Alginic acid is a linear copolymer of (1-4)-linked β-D-mannuronic acid (M-unit) and α-L-guluronic acid (G-unit) which units are linked together in different sequences or blocks. The monomers can appear in homopolymeric blocks of consecutive G-units (G-blocks), consecutive M-units (M-blocks), alternating M- and G-units (MG-blocks), or randomly organized blocks. Alginate is the salt of Alginic acid, for example sodium and/or calcium alginate. Alginic acid/alginate is extracted from seaweeds, such as giant kelp (*Macrocystis pyrifera*).

The gel contains the salt of a divalent cation, $Ca^{2+}$, $Mg^{2+}$, and/or $Zn^{2+}$, preferably $Ca^{2+}$. Examples of suitable gel-promoting salts include calcium carbonate, calcium phosphate, calcium hydrogen phosphate, and mixtures thereof. More than one salt of a divalent cation may be present.

Preferably, the gel comprises from 86 to 96 wt % water; preferably at least 87 wt %, preferably at least 88 wt %, preferably at least 89 wt %, preferably at least 90 wt %, preferably at least 91 wt %; preferably no more than 95 wt %, preferably no more than 94 wt %. Preferably, the gel comprises from 0.3 to 2.5 wt. % carboxymethylcellulose; preferably at least 0.5 wt %, preferably at least 0.6 wt %, preferably at least 0.7 wt %, preferably at least 0.8 wt %; preferably no more than 2 wt %, preferably no more than 1.5 wt %, preferably no more than 1.3 wt %. Preferably, the gel comprises from 0.3 to 2.5 wt. % Alginic acid, alginates, or mixtures thereof; preferably at least 0.5 wt %, preferably at least 0.6 wt %, preferably at least 0.7 wt %, preferably at least 0.8 wt %; preferably no more than 2 wt %, preferably no more than 1.5 wt %, preferably no more than 1.3 wt %. Preferably, the gel comprises from 0.1 to 1 wt % of a salt of calcium, magnesium or zinc, or a combination thereof; preferably at least 0.15 wt %, preferably at least 0.2 wt %, preferably at least 0.25 wt %; preferably no more than 0.8 wt %, preferably no more than 0.7 wt %, preferably no more than 0.6 wt %, preferably no more than 0.5 wt %, preferably no more than 0.4 wt %. Preferably the salt is a calcium salt.

Preferably, the gel comprises from 1 to 6 wt % of one or more fragrances; preferably at least 1.5 wt %, preferably at least 2 wt %; preferably no more than 5 wt %, preferably no more than 4.5 wt %, preferably no more than 4 wt %. Preferably, the fragrance is added to the gel at a temperature from 15 to 60° C., preferably from 15 to 50° C., preferably from 15 to 45° C.

Preferably, the gel comprises from 0.2 to 2 wt % of a nonionic surfactant; preferably at least 0.4 wt %, preferably at least 0.5 wt %, preferably at least 0.6 wt %, preferably at least 0.7 wt %; preferably no more than 1.8 wt %, preferably no more than 1.6 wt %, preferably no more than 1.4 wt %. More than one nonionic surfactant may be present. Preferably, the nonionic surfactant either (i) has the structure $RaO-(AO)_z—H$, wherein $R_a$ is aryl (e.g., phenyl), or linear or branched $C_6-C_{24}$ alkyl, AO at each occurrence is independently ethyleneoxy, propyleneoxy, butyleneoxy, or random or block mixtures thereof, and z is from 1 to 50; (ii) is an alkyl polyglucoside of the formula:

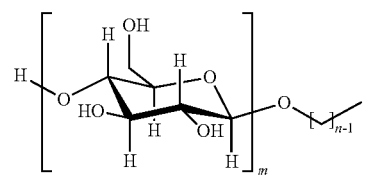

wherein m is from 1 to 10 and n is from 3 to 20; or (iii) is a polyethylene glycol HO—[—CH$_2$CH$_2$O—]$_n$-hydrogenated castor oil derivative, where n is from 20-60. The primary component of castor oil, the ricinoleate triglyceride, is ethoxylated. Preferably, AO is ethyleneoxy or propyleneoxy. Preferably, the nonionic surfactant comprises a C$_6$-C$_{18}$ alkyl group, an average of 2-8 moles polymerized units of propylene oxide and an average of 3-15 moles polymerized units of ethylene oxide. In a preferred embodiment, the nonionic surfactant has the following structure:

RO(CH$_2$CH(CH$_3$)O)$_x$(CH$_2$CH$_2$O)$_y$H where R is a C$_6$-C$_{12}$ alkyl group, x is from 3-7 and y is from 5-12. The numbers x and y are average values derived from a mixture of compounds. Preferably, R is a C$_6$-C$_{10}$ alkyl group, preferably C$_7$-C$_9$ alkyl group, preferably a C$_8$ alkyl group, preferably a 2-ethylhexyl group. Preferably, R is a branched alkyl group. Preferably, x is 4-6, preferably about 5. Preferably, y is 5-10, preferably 6-10, preferably 6-9, preferably 8-10, preferably about 9.

Preferably, the gel further comprises from 0.1 to 1 wt % glucono-delta-lactone; preferably at least 0.2 wt %, preferably at least 0.25 wt %, preferably at least 0.3 wt %, preferably at least 0.35 wt %; preferably no more than 0.9 wt %, preferably no more than 0.8 wt %, preferably no more than 0.7 wt %.

Preferably, the aqueous solution of a salt of calcium, magnesium or zinc which is applied to the surface of said gel has a concentration of the salt of calcium, magnesium or zinc from 2 to 20 wt %; preferably at least 3 wt %, preferably at least 4 wt %, preferably at least 5 wt %, preferably at least 6 wt %, preferably at least 7 wt %; preferably no greater than 16 wt %, preferably no greater than 14 wt %, preferably no greater than 13 wt %. Preferably, the amount of the aqueous solution applied to the surface is from 0.1 to 1 wt %; preferably at least 0.15 wt %, preferably at least 0.2 wt %, preferably at least 0.25 wt %; preferably no more than 0.8 wt %, preferably no more than 0.6 wt %, preferably no more than 0.5 wt %, preferably no more than 0.4 wt %. In one preferred embodiment of the invention, the additional aqueous solution of a salt of calcium, magnesium or zinc is coated on the inside of the mold prior to addition of the mixture of ingredients which will form the gel (gel precursor); if the mold is not closed and part of the gel surface is not in contact with the mold, additional aqueous solution of a salt of calcium, magnesium or zinc is applied to that part of the gel surface (e.g., by spraying, brushing, rolling, etc.), preferably at a temperature from 15 to 40° C., preferably 15 to 30° C. In another preferred embodiment of the invention, the formed gel is removed from the mold and the entire surface is then coated with the aqueous solution of a salt of calcium, magnesium or zinc. In this embodiment, preferably the solution is not applied to the mold.

Preferably, part of the carboxymethylcellulose, alginate and divalent metal salt are dissolved in water to form a first solution and part of the carboxymethylcellulose and the gluco-delta-lactone are dissolved in water to form a second solution. The solutions are combined, preferably by adding the first solution to the second solution. Preferably, the solutions are formed at a temperature from 20 to 85° C.; preferably at least 30° C., preferably at least 40° C., preferably at least 50° C., preferably at least 60° C.; preferably no more than 80° C., preferably no more than 75° C. Preferably, surfactant and fragrance are added to the combined aqueous solutions at a temperature from 15 to 60° C., preferably from 15 to 50° C., preferably from 15 to 45° C. Preferably, the gel is contacted with a salt of calcium, magnesium or zinc at a temperature from 15 to 40° C., preferably from 15 to 35° C., preferably from 15 to 30° C.

Without being bound by theory, it is believed that the method of this invention produces a gel having a higher degree of crosslinking near the surface.

Examples

Methods: TA Texture Analyzer

The TA.Texture Analyzer was used to perform tests in both tension and compression for cycling, flexure, constant strain and stress relaxation on such products as food, pharmaceuticals, cosmetics, packaging, leather, and adhesives. It has many built in test procedures to meet most product testing requirements and materials testing standards Hardness:

The Hardness value is the peak force that occurs during the first compression. The hardness need not occur at the point of deepest compression, although it typically does for most products.

Method for Normal Procedure for Air Gel Preparation (Table 1-3) Units in Grams:

1. Pre-blend Phase A ingredients by stirring together Ca salt; Na Alginate and carboxymethylcellulose (CMC)
2. Prepare Phase A by pre heating deionized water to 70° C., with stirring add all of phase A into vortex and continue stirring until uniform.
3. Pre-blend Phase B carboxymethylcellulose and gluco d-Lactone
4. Prepare phase B by heating deionized water to 70° C., with stirring add all of phase B into vortex and continue stirring until uniform.
5. Blend Phase B into Phase A. Gradually allow to cool about 30° C. (Approximately 60 min)
6. Add Phase C surfactant and fragrance oil with stirring into phase A/B.
7. Gradually cool to Room Temperature and pour into appropriate container for final gel set-up.

TABLE 1

Calcium Ion Study: Solidification of the air gel is dependent on the calcium ion salt chosen. To move away from CaHPO$_4$ due to legislation banning phosphate salts, an alternative salt with equal effectiveness is CaCO$_3$. Fragrances used included citrus jasmine and mandarin lily.

| Phase | | AG-A | AG-B | AG-C | AG-D | AG-E |
|---|---|---|---|---|---|---|
| A | Water | 122.22 | 119.52 | 122.36 | 121.72 | 121.04 |
| A | Calcium Hydrogen Phosphate | 0.78 | | | | |
| A | Calcium Citrate | | 3.28 | | | |
| A | Calcium Chloride | | | 0.64 | | |
| A | Calcium Tartrate | | | | 1.08 | |
| A | Calcium Lactate | | | | | 1.76 |

TABLE 1-continued

Calcium Ion Study: Solidification of the air gel is dependent on the calcium ion salt chosen.
To move away from CaHPO$_4$ due to legislation banning phosphate salts, an alternative salt with equal
effectiveness is CaCO$_3$. Fragrances used included citrus jasmine and mandarin lily.

| | | | | | | |
|---|---|---|---|---|---|---|
| A | Alginate | 2 | 2 | 2 | 2 | 2 |
| A | CMC MS$_{carboxy}$ = 0.5-1.2 | 1 | 1 | 1 | 1 | 1 |
| C | Citrus Jasmine | 10 | 10 | 10 | 10 | 10 |
| C | Surfactant A | 2 | 2 | 2 | 2 | 2 |
| B | Water | 60 | 60 | 60 | 60 | 60 |
| B | CMC MS$_{carboxy}$ = 0.5-1.2 | 1 | 1 | 1 | 1 | 1 |
| B | Gluco Lactone | 1 | 1 | 1 | 1 | 1 |
| | sum | 200.0 | 200.0 | 200.0 | 200.0 | 200.0 |
| | comments | well formed, solid gel | semi solid, sticky | not formed | Solid to semi, sticky | not formed |
| | TA Texture results, Hardness force in grams | 56.9 | NA | NA | NA | NA |

| Phase | | AG-A (R) | AG-F | AG-G | AG-H | AG-I | AG-J | AG-K | AG-L | AG-M |
|---|---|---|---|---|---|---|---|---|---|---|
| A | Water | 122.2 | 122.2 | 122.6 | 121.2 | 122.9 | 119.1 | 122.6 | 119.7 | 122.6 |
| A | Calcium Hydrogen Phosphate | 0.78 | | | | | | | | |
| A | Calcium Citrate | | | | | | 3.28 | | | |
| A | Calcium Tartrate | | | | 1.28 | 0.54 | | | | |
| A | Calcium Carbonate | | 0.78 | 0.39 | 0.39 | 0.39 | 0.39 | 0.39 | | 0.39 |
| A | Calcium Gluconate | | | | | | | | 1.23 | |
| A | Alginate | 2 | 2 | 2 | 2 | 2 | 2 | | 2 | 1 |
| A | CMC MS$_{carboxy}$ = 0.5-1.2 | 1 | 1 | 1 | 1 | 1 | 1 | 3 | 1 | 2 |
| C | Citrus Jasmine-Fragrance Oil | 10 | 10 | 10 | 10 | 10 | 10 | 10 | 10 | 10 |
| C | Surfactant .A | 2 | 2 | 2 | 2 | 2 | 2 | 2 | 2 | 2 |
| B | Water | 60 | 60 | 60 | 60 | 60 | 60 | 60 | 60 | 60 |
| B | CMC MS$_{carboxy}$ = 0.5-1.2 | 1 | 1 | 1 | 1 | 1 | 1 | 1 | 1 | 1 |
| B | Gluco Lactone | 1 | 1 | 1 | 1 | 1 | 1 | 1 | 1 | 1 |
| | sum | 200.0 | 200.0 | 200.0 | 200.0 | 200.0 | 200.0 | 200.0 | 200.0 | 200.0 |
| | comments | 3 hrs to set up well formed gel solid gel | 30 min set up well formed gel solid gel | 1.5 hrs set up well formed gel solid gel | not formed | 5-6 hrs set up well formed gel | semi solid | solid | semi solid | solid |
| | TA Texture Analyzer Results, Hardness force in grams | 54.7 | 52.3 | 48.1 | NA | 47.7 | NA | 50.3 | NA | 31.3 |

Surfactant A is 2-ethylhexyl with average 5 units PO capped with average 9 units EO

TABLE 2

Modifications were done with process aids and emulsifiers. The gel strength was altered and the set up time during processing was extended. Most changes interfered with the gelation structuring causing the gels to be weaker.

| Phase | | AG-N | AG-O | AG-P | AG-Q | AG-R |
|---|---|---|---|---|---|---|
| A | Water | 122.42 | 122.42 | 122.42 | 121.42 | 121.22 |
| A | Calcium Carbonate | 0.58 | 0.58 | 0.58 | 0.58 | 0.58 |
| A | Alginate | 2 | 2 | 2 | 2 | 2 |
| A | CMC $MS_{carboxy}$ = 0.5-1.2 | 1 | 1 | 1 | 3 | 3 |
| A | Polyethylene Oxide PEG-90M Mw 4,000,000 | | | | | 0.2 |
| C | Citrus Jasmine- Fragrance Oil | 10 | 10 | 10 | 10 | 10 |
| C | Surfactant. A | 2 | | | 2 | 2 |
| C | Alkyl PolyGlucoside | | 2 | | | |
| C | Polyethylene Glycol 40 Hydrogenated Castor Oil | | | 2 | | |
| B | Water | 60 | 60 | 60 | 60 | 60 |
| B | CMC $MS_{carboxy}$ = 0.5-1.2 | 1 | 1 | 1 | | |
| B | Gluco Lactone | 1 | 1 | 1 | 1 | 1 |
| | sum | 200.0 | 200.0 | 200.0 | 200.0 | 200.0 |
| | comments | Solid | Solid | semi solid | soft | semi solid |
| | TA Texture Analyzer Results, Hardness force in grams | 77.6 | 30.3 | 17.9 | 9.5 | 17.9 |

The external crosslinking enhanced the overall gel strength compared to non-coated gels.

TABLE 3

Carboxy methyl cellulose level and the degree of substitution variants are in the table below. Higher degree of substitution enhanced the gel structuring and strength.

| Phase | | AG-AI | AG-AJ | AG-AK | AG-AL | AG-AM |
|---|---|---|---|---|---|---|
| A | Water | 244.84 | 122.92 | 244.84 | 244.84 | 122.42 |
| A | Calcium Carbonate | 1.16 | 0.58 | 1.16 | 1.16 | 0.58 |
| A | Alginate | 4 | 2 | 4 | 4 | 2 |
| A | CMC $MS_{carboxy}$ = 0.5-1.2 | 2 | 1 | 2 | 2 | |
| A | CMC (Higher DS) $MS_{carboxy}$ = 1.0-1.5 | | | | | 1 |
| C | Mandarin Lily- Fragrance Oil | 20 | 10 | 20 | 20 | 10 |
| C | Surfactant A | 4 | 2 | 4 | 4 | 2 |
| B | Water | 120 | 60 | 120 | 120 | 60 |
| B | CMC $MS_{carboxy}$ = 0.5-1.2 | 2 | 1 | 2 | 2 | |
| B | Higher DS CMC $MS_{carboxy}$ = 1.0-1.5 | | | | | 1 |
| B | Gluco Lactone | 2 | 0.5 | 2 | 2 | 1 |
| | sum | 400.0 | 200.0 | 400.0 | 400.0 | 200.0 |
| | comments | Solid | soft | solid | solid | solid |
| | TA Texture Analyzer, Hardness force in grams | 72.6 | NA | 45.8 | 59.9 | 80.7 |

Process Variants can significantly alter the gel strength. Modification to Procedure for Air Gel Preparation, Units in Grams:
Procedure Variation (Samples Table 4-5)
  a. For Sample JT22, the normal procedure was separated out into each individual "solid" having its own Water solution. Therefore Carboxymethylcellulose $MS_{carboxy}$=0.5-1, Alginate, Surfactant. A, and GDL, all were separate solutions. This allowed us to mix each one until 100% dissolution was achieved, as each product has very different dissolution time.
  b. The samples JT23-JT24-JT25 in Table 4 were variations on the first. These sample runs had variable mix times to test when crosslink breakage became a significant problem in formulations. All separate solids were mixed until homogenous. Then "A" solutions were combined, and "B" solutions were combined. These phases were then mixed separately at variable times on the assumption that it was this crosslink formation stage that was the significant reaction phase for end product hardness. As such the mixing of A+C (fragrance/surfactant mixture), and AC+B were held constant.
  c. Sample JT23: phase A and phase B were separately mixed for 10 min. Then A & C combined and mixed for 5 min. Then A (+C) & B combined and mixed for 5 min.
  d. Sample JT24: phase A and phase B were separately mixed for 30 min. Then A & C combined and mixed for 5 min. Then A (+C) & B combined and mixed for 5 min.

Sample JT25: phase A and phase B were separately mixed for 60 min. Then A & C combined and mixed for 5 min. Then A (+C) & B combined and mixed for 5 min.

TABLE 4

Process variants

| Phase | Sample | JT22 | | JT23 | | JT24 | | JT25 g |
|---|---|---|---|---|---|---|---|---|
| A | CMC $MS_{carboxy}$ = 0.5-1.2 | 1.00 | CMC $MS_{carboxy}$ = 0.5-1.2 | 1.00 | CMC $MS_{carboxy}$ = 0.5-1.2 | 1.00 | CMC $MS_{carboxy}$ = 0.5-1.2 | 1.00 |
| A | alginate | 2.00 | alginate | 2.00 | alginate | 2.00 | alginate | 2.00 |
| A | calcium carbonate | 0.58 | calcium carbonate | 0.58 | calcium carbonate | 0.58 | calcium carbonate | 0.58 |
| A | Water | 122.4 | Water | 122.4 | Water | 122.4 | Water | 122.4 |
| C | Surfactant. A | 2.00 | surfactant A | 2.00 | surfactant A | 2.00 | surfactant A | 2.00 |
| C | fragrance oil | 10.00 | fragrance oil | 10.00 | fragrance oil | 10.00 | fragrance oil | 10.00 |
| B | Water | 60.00 | Water | 60.00 | Water | 60.00 | Water | 60.00 |
| B | CMC $MS_{carboxy}$ = 0.5-1.2 | 1.00 | CMC $MS_{carboxy}$ = 0.5-1.2 | 1.00 | CMC $MS_{carboxy}$ = 0.5-1.2 | 1.00 | CMC $MS_{carboxy}$ = 0.5-1.2 | 1.00 |
| B | Gluco Lactone | 1.00 | Gluco Lactone | 1.00 | Gluco Lactone | 1.00 | Gluco Lactone | 1.00 |
| Sum | | 200.00 | | 200.00 | | 200.00 | | 200.00 |
| | Separate water solutions then combine as normal | | A/B: 10 min A&C. oil: 5 min A&B: 5 min | | A/B: 30 min A&C. oil: 5 min A&B: 5 min | | A/B: 60 min A&C. oil: 5 min A&B: 5 min | |
| | TA Texture Analyzer, Hardness force in grams | 98.3 | | 17.8 | | 16.8 | | 11.6 |

TABLE 5

Carboxymethylcellulose, increased Molecular weight and degree of substitution.

| Phase | Sample | JT26 | | JT27 | | JT30 | |
|---|---|---|---|---|---|---|---|
| A | CMC $MS_{carboxy}$ = 1.0-1.5 | 1.00 | CMC $MS_{carboxy}$ = 1.0-1.5 | 1.00 | CMC $MS_{carboxy}$ = 0.5-1.2 increase Mw | 1.00 | |
| A | alginate | 2.00 | alginate | 2.00 | alginate | 2.00 | |
| A | Calcium Carbonate | 0.58 | Calcium Carbonate | 0.58 | Calcium Carbonate | 0.58 | |
| A | Water | 122.42 | Water | 122.42 | Water | 120.00 | |
| C | Surfactant A | 2.00 | Surfactant A | 2.00 | Surfactant A | 2.00 | |
| C | fragrance oil | 10.00 | Fragrance oil | 10.00 | Fragrance oil | 10.00 | |
| B | Water | 60.00 | Water | 60.00 | Water | 60.00 | |
| B | CMC $MS_{carboxy}$ = 1.0-1.5 | 1.00 | CMC $MS_{carboxy}$ = 1.0-1.5 | 1.00 | CMC $MS_{carboxy}$ = 0.5-1.2, increased Mw | 1.00 | |
| B | Gluco Lactone | 1.00 | Gluco Lactone | 1.00 | Gluco Lactone | 1.00 | |
| | Sum | 200.00 | | 200.00 | | 197.58 | |
| | Comments | solid | solid | solid | | solid | |
| | TA Texture Analyzer, Hardness force in grams | 46.40 | | 60.2 | | 64.5 | |

TABLE 6

(Sample ID AG-AI referenced in Table 3), units in gram: Stability testing at various conditions and temperatures: Freeze Thaw repeated 5 times by placing samples in freezer at −10° C. overnight, removing in morning, thawing during the day and placing back into freezer the next evening. % weight loss determined based on initial weight of sample.

| | Days at RT (Room Temperature) | | | | |
|---|---|---|---|---|---|
| | 0 | 3 | 7 | 14 | 28 |
| wgt loss AG-AI | 50.36 | 47.64 | 43.49 | 41.84 | 40.62 |
| % wgt loss AG-AI | 0.00 | 5.40 | 13.64 | 16.92 | 19.34 |
| wgt loss AG-AI $CaCl_2$ | 52.55 | | 52.50 | 51.49 | 38.70 |
| % wgt loss AG-AI $CaCl_2$ | 0.00 | | 0.10 | 2.02 | 26.36 |

| | Cycles 5 F/T (Freeze/Thaw)* | | | | |
|---|---|---|---|---|---|
| | 0 | 1 | 2 | 3 | 4 |
| wgt loss AG-AI | 49.48 | 49.54 | 47.72 | 47.53 | 41.20 |
| % wgt loss AG-AI | 0.00 | 0.00 | 3.56 | 3.94 | 16.73 |
| wgt loss AG-AI $CaCl_2$ | 45.05 | | 43.10 | 42.90 | 41.02 |
| % wgt loss AG-AI $CaCl_2$ | 0.00 | 0.00 | 4.33 | 4.77 | 8.95 |

| | Days at 3° C. | | | | |
|---|---|---|---|---|---|
| | 0 | 3 | 7 | 14 | 28 |
| | 0 | 3 | 7 | 14 | 28 |
| wgt loss AG-AI | 46.73 | 46.48 | 44.91 | 44.58 | 42.45 |
| % wgt loss AG-AI | 0.00 | 0.53 | 3.89 | 4.60 | 9.16 |
| wgt loss AG-AI $CaCl_2$ | 56.30 | | 51.37 | 50.96 | 48.57 |
| % wgt loss AG-AI $CaCl_2$ | 0.00 | | 8.76 | 9.48 | 13.73 |

| | Days at 40° C. | | | | |
|---|---|---|---|---|---|
| | 0 | 3 | 7 | 14 | 28 |
| wgt loss AG-AI | 51.13 | 49.26 | 44.66 | 41.52 | 23.24 |
| % wgt loss AG-AI | 0.00 | 3.66 | 12.65 | 18.80 | 54.55 |
| wgt loss AG-AI $CaCl_2$ | 58.39 | | 51.36 | 48.75 | 37.18 |
| % wgt loss AG-AI CaCl2 | 0.00 | | 12.04 | 16.51 | 36.32 |

| | Days at 50° C. | | | | |
|---|---|---|---|---|---|
| | 0 | 3 | 7 | 14 | 28 |
| wgt loss AG-AI | 46.26 | 42.46 | 31.93 | 27.22 | 4.16 |
| % wgt loss AG-AI | 0.00 | 8.21 | 30.98 | 41.16 | 91.01 |
| wgt loss AG-AI $CaCl_2$ | 43.49 | 37.53 | 36.43 | 33.32 | 3.86 |
| % wgt loss AG-AI $CaCl_2$ | 0.00 | 13.70 | 16.23 | 23.38 | 91.12 |

Fragrance Longevity was tracked vs time using four fragrance trackers from the perfume. The fragrance trackers chosen: Ethyl butyrate, Ethyl 2-methylbutyrate, Dihydromyrcenol, and Linalool. Two were high notes with high volatility and two were lower notes with lower volatility. These were tracked over two months. Results indicate that all four fragrance trackers were still available from the air gel with the lower volatility being predominately unchanged from their initial values. This is significantly better than commercial air gels currently on the market that last 2-3 weeks. See charts below. The last chart indicates the fragrance loss at 2 week and 4 week aging of the samples treated externally with $CaHPO_4$ vs samples that were not treated externally with $CaHPO_4$. Specifically the samples with external treatment appear to withhold or contain the fragrance longer than the samples without it.

Fragrance trackers monitored with time in Table 7 to 11.
Procedure for Fragrance Trackers Using GC-MS:
A 1% standard mix of the fragrance trackers was prepared in toluene. The std mix was diluted in toluene to make the following concentrations: 10,000 and 1000, 500, 100, 10, and 1 ppm. Each standard were injected into a microvial in a TDU (thermal desorption tube) directly into the TDU. A calibration curve was made for each standard Sample size: 5 grams
Analysis by Headspace GC-MS
Heat to 33° C. for 0.5 min of heating prior to introduction into GC-MS (to understand VOCs that might contribute to odor
Use Column: DB-Wax (30 m×0.25 mm×0.50 μm)
Analysis by GC-MS-Olfactory
VOCs were collected by inserting a SPME fiber through the septum of a 22 mL headspace vial containing the air gels. SPME (Solid-phase microextraction) collection, 1-4 hours at room temperature, SPME injected into the hot injection port of the GC-MS-O. Analysts sniffed the GC effluent as it eluted from the GC column and recorded the retention time of the odor markers. The Column: Rtx-5MS (30 m×0.25 mm×0.25 μm). Units are ppm, vol/vol

TABLE 7

Ethyl butyrate levels over time

| weeks | 0 | 1 | 2 | 3 | 4 | 8 |
|---|---|---|---|---|---|---|
| Fresh Gel- small vial | 11 | 0.6 | 0.04 | 0 | 0 | 0 |
| Fresh gel - large sample | 21 | 6 | 3 | 1 | 0.3 | 0 |
| 4 months aged gel - large sample | 5 | 0.9 | 0.3 | 0.5 | 0.0 | 0 |

TABLE 8

Ethyl 2-methylbutyrate levels over time

| weeks | 0 | 1 | 2 | 3 | 4 | 8 |
|---|---|---|---|---|---|---|
| Fresh Gel- small vial | 126 | 24 | 4 | 0.5 | 0.1 | 0 |
| Fresh gel - large sample | 239 | 84 | 52 | 35 | 22 | 1.0 |
| 4 months aged gel - large sample | 121 | 24 | 11 | 37 | 3 | 0 |

TABLE 9

Dihydromyrcenol levels over time

| weeks | 0 | 1 | 2 | 3 | 4 | 8 |
|---|---|---|---|---|---|---|
| Fresh Gel- small vial | 9 | 10 | 10 | 9 | 9 | 7 |
| Fresh gel - large sample | 11 | 10 | 11 | 9 | 10 | 8 |
| 4 months aged gel - large sample | 13 | 10 | 12 | 11 | 11 | 9 |

TABLE 10

Linalool levels over time

| weeks | 0 | 1 | 2 | 3 | 4 | 8 |
|---|---|---|---|---|---|---|
| Fresh Gel- small vial | 9 | 10 | 11 | 10 | 9 | 7 |
| Fresh gel - large sample | 11 | 10 | 12 | 10 | 10 | 8 |
| 4 months aged gel - large sample | 12 | 10 | 11 | 11 | 10 | 8 |

TABLE 11

Effect of external CaCl$_2$ on fragrance trackers, with time.

| Compounds | 2 wk aging No CaCl$_2$ sprayed externally | 2 wk aging with CaCl$_2$ sprayed externally | 4 wk aging No CaCl$_2$ sprayed externally | 4 wk aging with CaCl$_2$ sprayed externally |
|---|---|---|---|---|
| Ethyl butyrate | 2 | 3 | 1.2 | 0.3 |
| Ethyl 2-methylbutyrate | 26 | 52 | 15 | 22 |
| Dihydromyrcenol | 0.9 | 11 | 1.4 | 10 |
| Linalool | 0.8 | 12 | 1.4 | 10 |

The invention claimed is:

1. A method for producing a crosslinked gel; said method comprising steps of:
combining (i) water, (ii) alginic acid, alginates, or mixtures thereof, (iii) carboxymethylcellulose, (iv) a salt of calcium, magnesium or zinc, (v) a nonionic surfactant and (vi) fragrance to form a combination;
introducing the combination into a mold to form a gel having a surface;
removing a formed gel having a surface from the mold; and
then contacting the surface of said gel with an additional aqueous solution of a salt of calcium, magnesium or zinc.

2. The method of claim 1 in which the gel comprises from 86 to 96 wt % water, from 0.3 to 2.5 wt. % carboxymethylcellulose; from 0.3 to 2.5 wt. % alginic acid, alginates, or mixtures thereof; from 0.1 to 1 wt % of a salt of calcium, magnesium or zinc, or a combination thereof; from 0.2 to 2 wt % nonionic surfactant and from 1 to 6 wt % of one or more fragrances; and wherein the additional aqueous solution is added in an amount from 0.1 to 1 wt % and wherein the additional aqueous solution comprises from 2 to 20 wt % of a salt of calcium, magnesium or zinc.

3. The method of claim 2 in which the salt is a calcium salt.

4. The method of claim 3 in which the carboxymethylcellulose has a molar degree of substitution $MS_{carboxy}$ of from 0.3 to 1.8.

5. The method of claim 4 in which the gel comprises from 90 to 95 wt % water, from 0.6 to 1.5 wt. % carboxymethylcellulose; from 0.6 to 1.5 wt. % alginic acid, alginates, or mixtures thereof; from 0.2 to 0.7 wt % of a calcium salt; from 0.4 to 1.8 wt % nonionic surfactant and from 1.5 to 6 wt % of one or more fragrances; and wherein the additional aqueous solution is added in an amount from 0.15 to 0.5 wt % and wherein the additional aqueous solution comprises from 3 to 14 wt % of a salt of calcium, magnesium or zinc.

6. The method of claim 5 in which the surface of the gel is contacted with the additional aqueous solution at a temperature from 15 to 35° C.; wherein the additional aqueous solution comprises a calcium salt.

* * * * *